(12) United States Patent
Oiwa (10) Patent No.: US 11,471,569 B2
(45) Date of Patent: Oct. 18, 2022

(54) MEDICAL DEVICE

(71) Applicant: TERUMO KABUSHIKI KAISHA, Tokyo (JP)

(72) Inventor: Tomoya Oiwa, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 554 days.

(21) Appl. No.: 16/575,570

(22) Filed: Sep. 19, 2019

(65) Prior Publication Data

US 2020/0023101 A1 Jan. 23, 2020

Related U.S. Application Data

(63) Continuation of application No. PCT/JP2018/012148, filed on Mar. 26, 2018.

(30) Foreign Application Priority Data

Mar. 30, 2017 (JP) .............................. JP2017-067868

(51) Int. Cl.
*A61L 24/04* (2006.01)
*A61L 31/10* (2006.01)
(Continued)

(52) U.S. Cl.
CPC .............. *A61L 31/10* (2013.01); *A61L 31/082* (2013.01); *A61L 31/16* (2013.01);
(Continued)

(58) Field of Classification Search
CPC ................................................... A61L 2420/04
See application file for complete search history.

(56) References Cited

U.S. PATENT DOCUMENTS 7,695,753 B2 * 4/2010 Pursley ................ B05D 3/0209
427/421.1
8,900,652 B1 * 12/2014 Caballero ................ B05D 7/02
604/103.08
(Continued)

FOREIGN PATENT DOCUMENTS

CN 1351097 A 5/2002
CN 101618249 A 1/2010
(Continued)

OTHER PUBLICATIONS

Zhang et al. "Coatings and Coating Techniques", Chemical Industry Press, (Jan. 31, 2006) pp. 181-189 (Year: 2006).*
(Continued)

*Primary Examiner* — Cachet I Proctor
(74) *Attorney, Agent, or Firm* — Buchanan Ingersoll & Rooney PC (57) ABSTRACT

The disclosed medical device has high visibility on non-woven fabric having a color such as green, blue, or the like, excellent identifiability from other medical devices having colors such as green, blue, or the like, and also a high adhesion property and strength of a coating. The medical device comprises an elongated body and a resin layer covering at least a proximal portion of the elongated body. The resin layer is comprised of a first layer which includes a first fluororesin, an organic pigment and titanium oxide, and a second layer which is formed on the first layer and includes a second fluororesin.

18 Claims, 2 Drawing Sheets

(51) Int. Cl.
  *A61L 31/08*   (2006.01)
  *A61L 31/16*   (2006.01)

(52) U.S. Cl.
  CPC ..... *A61L 2300/442* (2013.01); *A61L 2420/02* (2013.01); *A61L 2420/06* (2013.01); *A61L 2420/08* (2013.01)

(56) References Cited

U.S. PATENT DOCUMENTS

| | | | |
|---|---|---|---|
| 2008/0228109 A1 | 9/2008 | Kinoshita et al. | |
| 2009/0053527 A1 | 2/2009 | Iwamori et al. | |
| 2009/0211909 A1 | 8/2009 | Nesbitt | |
| 2009/0312745 A1* | 12/2009 | Goldfarb | A61B 17/24 |
| | | | 604/514 |
| 2010/0004561 A1* | 1/2010 | Nabeshima | A61M 25/09 |
| | | | 600/585 |
| 2011/0015279 A1 | 1/2011 | Doerr et al. | |
| 2011/0125253 A1 | 5/2011 | Casanova et al. | |
| 2011/0152791 A1 | 6/2011 | Kobayashi | |
| 2011/0244147 A1 | 10/2011 | Wang et al. | |
| 2011/0305909 A1* | 12/2011 | Weaver | C09D 5/1693 |
| | | | 427/322 |
| 2017/0303891 A1* | 10/2017 | Yamashita | B29C 48/0018 |
| 2018/0207399 A1* | 7/2018 | Chou | A61M 25/09 |

FOREIGN PATENT DOCUMENTS

| | | |
|---|---|---|
| CN | 101918070 A | 12/2010 |
| CN | 102112175 A | 6/2011 |
| CN | 102256803 A | 11/2011 |
| CN | 102617913 A | 8/2012 |
| JP | 2002201425 A | 7/2002 |
| JP | 2009514655 A | 4/2009 |
| JP | 2015100664 A | 6/2015 |
| WO | 2010018762 A1 | 2/2010 |

OTHER PUBLICATIONS

BYK DISPERBYK-110—Product Data , Palmer Holland technical datasheet, Oct. 2012 (Year: 2012).*
BYK "Anti-TERRA-204". BYK additives & Instruments. Sep. 2012. byk.com/additives (Year: 2012).*
Office Action (Examination Report) dated Sep. 15, 2020, by the Intellectual Property India in corresponding India Patent Application No. 201917038005 with an English Translation of the Office Action. (5 pages).
Office Action (Notice of Refusal) dated Jun. 29, 2021, by the National Bureau of Knowledge and Property of the People's Republic of China in corresponding Chinese Patent Application No. 201880020081.8 and an English Translation of the Office Action. (18 pages).
International Search Report (PCT/ISA/210) and translation and Written Opinion (PCT/ISA/237) dated May 29, 2018, by the Japanese Patent Office as the International Searching Authority for International Application No. PCT/JP2018/012148.
Office Action (The First Office Action) dated Apr. 2, 2021, by the State Intellectual Property Office of People's Republic of China in corresponding Chinese Patent Application No. 201880020081.8, and an English Translation of the Office Action. (19 pages).
U.S. Appl. No. 16/575,864, filed Sep. 19, 2019, Oiwa.

* cited by examiner

FIG. 2

MEDICAL DEVICE

CROSS-REFERENCES TO RELATED APPLICATIONS

This application is a continuation of International Application No. PCT/JP2018/012148 filed on Mar. 26, 2018, and claims priority to Japanese Patent Application No. 2017-067868 filed on Mar. 30, 2017, the entire content of both of which is incorporated herein by reference.

TECHNICAL FIELD

The present invention generally relates to a medical device and method for fabricating or producing a medical device.

BACKGROUND ART

A guide wire is a medical device which is employed for guiding a catheter used for percutaneous transluminal coronary angioplasty (PTCA), cardiovascular imaging test, or the like for treatment of a stenosis in coronary artery of heart. As a part of percutaneous transluminal coronary angioplasty, the guide wire is inserted in combination with a balloon catheter, in a state in which the guide wire protrudes beyond the distal end of the balloon catheter, to the vicinity of a stenosis in coronary artery as a target site. In the stenosis, only the thin guide wire passes through first to widen the stenosis, thus guiding the balloon catheter.

For the purpose of having easy movement in blood vessel or easy passage through a lesion or the like and also enhancing the sliding property to reduce the resistance with an inner wall of a catheter, it is typical for the guide wire that a resin layer such as fluororesin or the like is coated around a core member such as alloy or the like.

Accordingly, a medical device such as catheter, guide wire, or the like that is inserted to a lumen of a living body like airway, respiratory tract, gastrointestinal tract, urinary tract, blood vessel, or the like or a tissue is required to have an operability which enables clear insertion to a target site without damaging tissue. Furthermore, the medical device is also required to exhibit an excellent sliding property so as to avoid a damage on mucosal membrane caused by friction or an occurrence of inflammation while the medical device is held in tissue.

Meanwhile, since the medical device to be inserted to a lumen or a tissue of a living body has a small diameter, it may be sometimes difficult to immediately visually recognize the medical device in an operation room. As such, according to Japanese Application Publication No. 2015-100664, the visibility of a guide wire is increased by including a green inorganic pigment such as chromium oxide, cobalt green, or the like contained in a resin layer to impart coloration to the guide wire.

SUMMARY

In an operation room in which percutaneous transluminal coronary angioplasty or the like is performed, non-woven fabric like surgical drape, cover for an instrument table, a gown, or the like is used. The color of the non-woven fabric is either green or blue in most cases. If a medical device has a color hue which belongs to the same color group as the non-woven fabric, the medical device and background color would have the same color so that there may be a case in which a doctor has a difficulty visually recognizing the medical device immediately. Accordingly, the guide wire should have various colors without being limited to green or blue described above.

Furthermore, for percutaneous transluminal coronary angioplasty, plural guide wires may be used simultaneously depending on the type of lesion, a bending property, or the like. For a procedure in which plural medical devices are used simultaneously, it is preferable that a doctor can identify each medical device by a handle part. For a guide wire, a method for identifying each guide wire by forming a marker near a proximal portion of a guide wire is known. However, due to the long length of a guide wire, the handle part for a doctor is quite apart from the proximal portion of a guide wire so that a work involved in confirming the marker at the proximal portion of a guide wire would be burdensome to a doctor. Accordingly, to identify each medical device by a handle part, the guide wire is required to have various colors within a range in which the handle part for a doctor is included.

To enhance the visibility and identifiability of a medical device by a doctor, the medical device is preferably colored with a color such as red or the like that has high visibility and can be identified relative to green or blue. For example, for a guide wire, a method of coloring a guide wire by forming a coating containing fluororesin layer, which is blended with an organic pigment representing red, on an outer surface of a core member (elongated body) of a guide wire may be considered. The fluororesin layer on an outer surface of the core member (elongated body) of the guide wire is generally formed by coating the coating solution containing the fluororesin dispersed in a solvent on the core member and then performing baking.

However, in general, since baking for forming a fluororesin layer on an outer surface of a core member of a guide wire is carried out at high temperatures, there has been a case in which the organic pigment is discolored, thus impairing the color-exhibition property of a resin layer. Furthermore, when the coating includes large amounts of an organic pigment relative to the fluororesin, it is necessary that the dispersant for dispersing the organic pigment is also blended in large amounts. With the dispersant blended in large amounts, there has been a case in which the adhesion property of the fluororesin layer to a core member and to other resin layer to be laminated is impaired, and thus the coating is easily peeled off.

The medical device disclosed here has high visibility on non-woven fabric having a color such as green, blue, or the like, excellent identifiability from other medical devices having colors such as green, blue, or the like, and also a high adhesion property and strength of a coating.

One aspect of the disclosure here involves a medical device comprising an elongated body and a resin layer covering at least a proximal portion of the elongated body, wherein the resin layer has a first layer which includes a first fluororesin, an organic pigment and titanium oxide, and a second layer which is formed on the first layer and includes a second fluororesin.

According to another aspect, a medical device comprises an elongated body possessing a distal-most end, a proximal-most end, and a distal portion extending from the distal-most end of the elongated body towards the proximal-most end of the elongated body. A first resin layer covers the proximal portion of the elongated body and does not cover the distal portion of the elongated body. The first resin layer includes a first fluororesin, organic pigment, and titanium oxide. A second resin layer covers the first resin layer and does not cover the distal portion of the elongated body, and the second resin layer includes a second fluororesin. The composition of the first resin layer differs from the composition of the second resin layer.

In accordance with another aspect, a method for producing a medical device comprises: coating a first coating solution on at least a proximal portion of an elongated body to form a first coating film on the proximal portion of the elongated body, wherein the first coating solution that is coated on the proximal portion of the elongated body to form the first coating film includes a first fluororesin, organic pigment, and titanium oxide; coating a second coating solution on the first coating film to form a second coating film, wherein the second coating solution that is coated on the first coating film to form the second coating film including a second fluororesin; and baking the elongated body coated with the first and second coating films at a temperature equal to or higher than a melting point of the first fluororesin and a melting point of the second fluororesin.

DETAILED DESCRIPTION

Generally speaking, one embodiment of a medical device according to the disclosure here may comprise an elongated body and a resin layer covering at least a proximal portion of the elongated body, in which the resin layer has a first layer which includes a first fluororesin, an organic pigment and titanium oxide, and a second layer which is formed on the first layer and includes a second fluororesin.

By forming a resin layer (first layer) on an elongated body with the combined use of an organic pigment and titanium oxide, heat resistance of the resin layer (first layer) is enhanced due to the high heat resistance of titanium oxide, and thus discoloration of an organic pigment caused by baking (curing) is suppressed. Furthermore, even when the organic pigment is slightly discolored, as titanium oxide present near the organic pigment exhibits white, brightness of the color is maintained at high level. Accordingly, the color-exhibition property of the resin layer (first layer) is favorable, and thus a coating which exhibits high visibility on non-woven fabric having a color such as green, blue, or the like, and has excellent identifiability (i.e., is relatively easily distinguishable) from other medical devices having colors such as green, blue, or the like is obtained. That is, the medical device is quite visible against non-woven fabric that is colored green, blue, or the like, and is also quite distinguishable from other medical devices that are colored green, blue, or the like.

Furthermore, with the combined use of an organic pigment and titanium oxide, the resin layer (first layer) exhibits a favorable color-exhibition property even when the blending amount of an organic pigment is small. Due to this reason, it may be sufficient to have only a small amount of a dispersant that is required for dispersing the organic pigment and titanium oxide, or the dispersant may not be necessary. Accordingly, the adhesion property of the resin layer (first layer) to core member, or to other resin layer (for example, the second layer) laminated on the first layer is not lowered or reduced by the dispersant, and thus the adhesion property of a coating is favorable. Furthermore, the mechanical strength of the resin layer is enhanced by blending titanium oxide as an inorganic filler, and thus the strength of the coating is increased.

The medical device having the above coating is a device which has high visibility on non-woven fabric having a color such as green, blue, or the like, excellent identifiability or distinguishability from other medical devices having colors such as green, blue, or the like, and also high adhesion property and strength of a coating.

Hereinbelow, embodiments of the medical device representing examples of the inventive medical device disclosed here are described. The present invention is not limited to the following embodiments.

In the present specification, the expression "X to Y" indicating a range includes X and Y, and means "X or more and Y or less". Furthermore, in the present specification, unless particularly described otherwise, operations and measurements of physical properties and the like are performed under conditions at room temperature (20° C. or higher and 25° C. or lower) and relative humidity (RH) of 40% RH or more and 50% RH or less.

The medical device according to the present embodiment is a medical device that is used after insertion into a living body, for example, and, specifically, examples of the medical device include catheters such as an indwelling needle, an IVH catheter, a thermo-dilution catheter, a angiographic catheter, a dilatation catheter (for example, a PTCA catheter), a dilator, an introducer, and the like which are inserted into or caused to indwell in a blood vessel, or a guide wire and a stylet for these catheters; catheters such as a gastric tube catheter, a nutritional catheter, a tube for tube-feeding nutrition (ED), and the like which are orally or nasally inserted into or caused to indwell in a digestive organ; catheters such as an oxygen catheter, an oxygen cannula, a tube or a cuff of an endotracheal tube, a tube or a cuff of a tracheotomy tube, an endotracheal suction catheter, and the like which are orally or nasally inserted into or caused to indwell in the airway or the trachea; catheters such as a urethral catheter, a catheter for guiding urine, a catheter or a balloon of a urethral balloon catheter, and the like which are inserted into or caused to indwell in the urethra or the ureter; catheters such as a suction catheter, a drainage catheter, a rectum catheter, and the like which are inserted into or are caused to indwell in various types of body cavities, internal organs, and tissues; an artificial trachea and an artificial bronchus; medical devices (an artificial lung, an artificial heart, an artificial kidney, and the like) for extracorporeal circulation treatment or circuits thereof; medical devices such as an endoscope which is inserted into various types of organs and is required to have low frictional resistance with respect to the outer surface and the like of a living body when being inserted into, being caused to slide into, and being caused to indwell in the living body; and the like.

Among them, the medical device is preferably a catheter or a guide wire, and is particularly preferably a guide wire.

Figure 1:
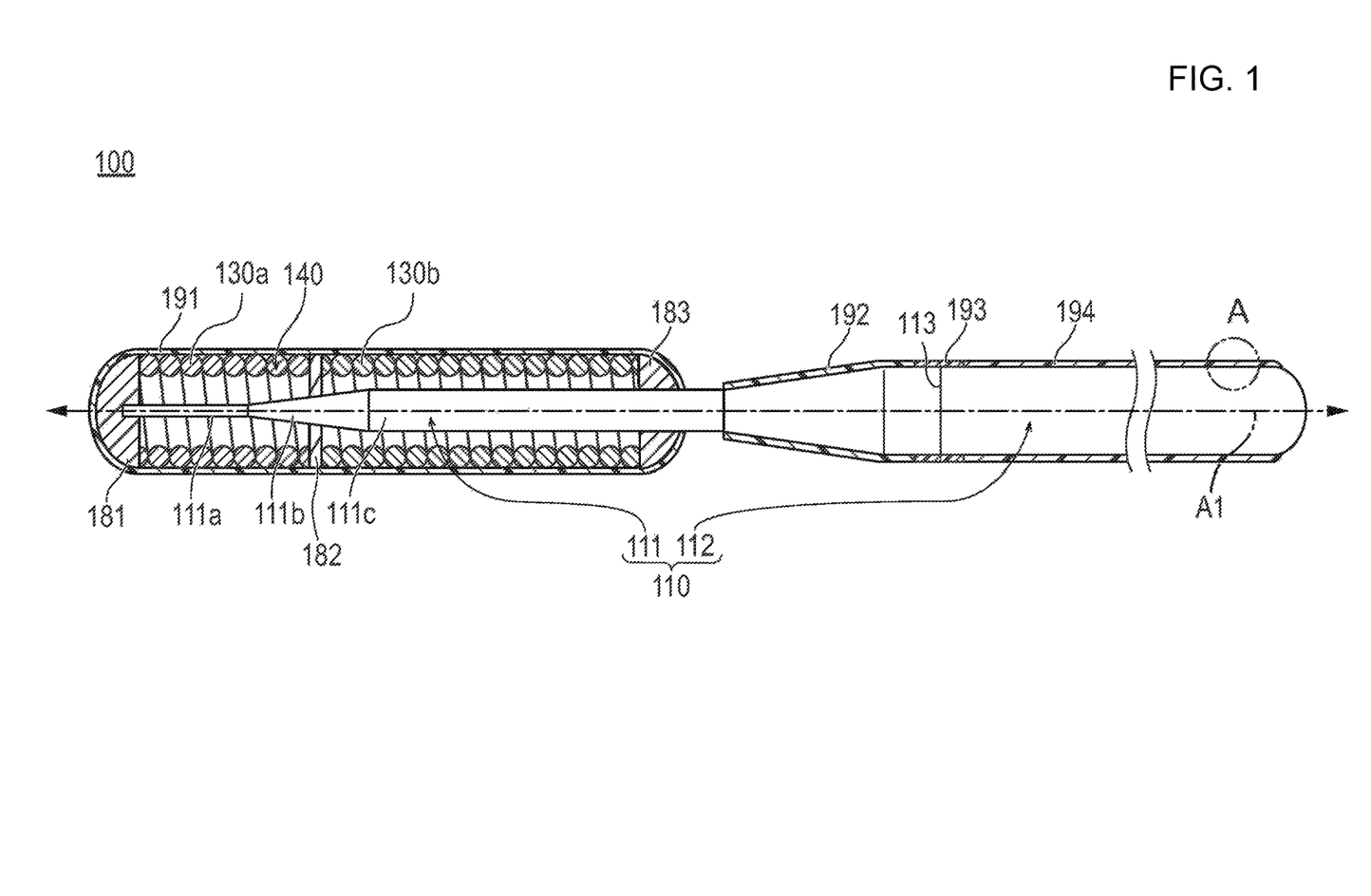
FIG. 1 is a partial longitudinal cross-sectional view illustrating a guide wire (cross-sectional view along the axial direction of guide wire).

The description below describes an example in which the medical device is a guide wire such as shown in FIG. 1. The dimensional ratio of the drawings is exaggerated for the sake of convenience for description, and it may be different from the actual ratio.

FIG. 1 is a partial longitudinal cross-sectional view illustrating the guide wire 100 (cross-sectional view along the axial direction of guide wire 100).

As illustrated in FIG. 1, the guide wire 100 has an elongated core portion (core wire) 110 having flexibility and a wire member 140 wound in a spiral shape so that the wound wire member 140 is in surrounding but spaced relation to a part of the core wire 110. The wound wire member 140 is comprised of a first coil portion 130*a* and a second coil portion 130*b* that are disposed to cover at least the distal portion of the core portion 110. That is, the distal portion of the core portion 110 and the wound wire member 140 (the first and second coil portions 130*a*, 130*b*) axially overlap one another. Furthermore, as illustrated in FIG. 1, on an outer surface of the guide wire 100, resin layers 191, 192, 193, and 194 to be described later are formed in this order from the distal end side. Furthermore, the illustration of the resin layer does not necessarily indicate an embodiment in which the aforementioned four resin layers 191, 192, 193, 194 are adjacent to each other, and other resin layers or an exposed portion of the core wire having no resin layer may be included between each axially adjacent resin layer. Furthermore, the medical device is not limited to an embodiment in which the aforementioned four resin layers are necessarily provided, and at least one resin layer of the resin layers 191, 192, and 193 may not be included (i.e., at least one of the resin layers 191, 192, 193 may be excluded). Furthermore, it is possible to increase the resin layer(s), for example, each resin layer may be formed of two or more resin layers that are different from each other.

In the following description, the length direction of the core portion 110 (left and right direction in FIG. 1) is defined as the axial direction, and it is identified by the arrow A1 in each drawing. Furthermore, the side or end of the guide wire 100 which is introduced into a living body (into a blood vessel) is defined as a distal end side or distal end (distal side, left side of FIG. 1), and the end or side opposite to the distal end side is defined as a proximal end side or proximal end (proximal side, right side of FIG. 1). Furthermore, the distal portion described in the present specification means a portion which includes a certain range in the axial direction from the distal end (distal-most end), while the proximal portion means a portion which includes a certain range in the axial direction from the proximal end (proximal-most end). In that case, the proximal portion does not necessarily include the proximal end (proximal-most end).

The core portion 110 is an elongated body having a first elongated core portion 111 disposed on the distal end side in the axial direction and a second elongated core portion 112 disposed on the proximal end side of the first core portion 111 and bonded (fixed) to the first core portion 111. The total length of the core portion 110 may preferably be 500 to 5000 mm, though is not limited in this regard. In particular, the core portion 110 of a guide wire used for PTCA generally has total length of 1700 to 3000 mm.

The first elongated core portion 111 has an elongated flat plate-shaped flat plate portion 111*a* which is disposed on the distal end side of the first core portion, an elongated tapered portion 111*b* which extends from the flat plate portion 111*a* toward the proximal end side, and an elongated constant outer diameter portion 111*c* which extends, at roughly constant outer diameter, from the tapered portion 111*b* toward the proximal end side. As shown in FIG. 1, in the illustrated embodiment, the tapered portion 111*b* extends immediately from the proximal-most end of the flat plate portion 111*a*, and the constant outer diameter portion 111*c* extends immediately from the proximal-most end of the tapered portion 111*b*. Furthermore, the shape of the first core portion 111 is not limited to the illustrated shape. The first core portion 111 may be also formed to have a constant outer shape (constant outer diameter) from the distal end side toward the proximal end side, for example. Furthermore, it is also possible that the core portion 110 is not constituted by plural members like the first core portion 111 and the second core portion 112. Instead, the core portion 110 may be constituted by a single continuous member, for example. As for the width and thickness of the flat plate portion 111*a*, the width may be 0.1 to 0.5 mm or so and the thickness may be 0.01 to 0.1 mm or so, for example. Furthermore, the outer diameter of the constant outer diameter portion 111*c* may be 0.2 to 1 mm or so, for example.

Materials for constituting the first core portion 111 and the second core portion 112 are not particularly limited, but various metal materials such as Ni—Ti based alloy, stainless steel such as SUS302, SUS304, SUS303, SUS316, SUS316L, SUS316J1, SUS316J1L, SUS405, SUS430, SUS434, SUS444, SUS429, SUS430F or the like, a piano wire, a cobalt-based alloy, and super-elastic alloy or the like can be used for each, for example. Among them, the material for constituting the first core portion 111 is preferably Ni—Ti based alloy, and the material for constituting the second core portion 112 is preferably stainless steel. The material for constituting the second core portion 112 may be the same or different from the material constituting the first core portion 111. The first core portion 111 and the second core portion 112 may be bonded by a bonding portion or fixing portion 113 according to a method that includes welding or the like, for example.

A first coil portion 130*a* and a second coil portion 130*b* (hereinbelow, they are also collectively referred to as a coil portion 130) are disposed so as to cover or surround, within a certain range in the axial direction, the first core portion 111. The coil portion 130 is constituted by the wire member 140 which is wound in spiral shape along the peripheral direction of the core portion 110 while having the core portion 110 (the first core portion 111) at the center.

The wire member 140 has an approximately cylindrical shape, with a lumen formed in the inside (i.e., the wound wire member 140 surrounds a lumen) to accommodate the first core portion 111.

The inner diameter and outer diameter of the coil portion 130 are constant, inclusive of substantially constant, along the axial direction. Furthermore, the length of the coil portion 130 in the axial direction, as well as the outer diameter and the inner diameter of the coil portion 130, are not particularly limited, and they can be suitably set depending on the product specification or the like of the guide wire 100.

The first coil portion 130*a* is fixed, via a first fixing portion 181 and a second fixing portion 182, on the periphery of the flat plate portion 111*a* and the tapered portion 111*b* of the first core portion 111, respectively. The second coil portion 130*b* is fixed, via the second fixing portion 182 and a third fixing portion 183, on the periphery of the tapered portion 111*b* and the constant outer diameter portion 111*c* of the first core portion 111, respectively. Each of the fixing portion 181, 182, and 183 may be constituted by solder, brazing material, adhesive, or the like. In consideration of an influence on a lumen of a living body such as blood vessel or the like, the distal end surface of the first fixing portion 181 preferably has a rounded shape as illustrated. The second fixing portion 182 is located at the tapered portion 111*b* of the first core portion 111.

The material for constituting the wire member 140 to form the coil portion 130 is not particularly limited, and stainless steel, super-elastic alloy, cobalt-based alloy, metal such as gold, platinum, tungsten, or the like, or alloys containing these materials, and the like can be used. It is also possible that, for the coil portion 130, the distal portion and proximal portion thereof are constituted of different materials, for example. For example, the first coil portion 130a may be formed of a material having a radio-opaque property (for example, platinum), or the like, while the second coil portion 130b may be formed of a material which transmits X-rays more easily compared to the distal portion (for example, stainless steel). FIG. 1 shows that the cross-section of a wire member in the coil portion 130 has a round shape, but the wire member forming the coil portion 130 may also possess an elliptical cross-section, a rectangular cross-section, or the like.

As illustrated in FIG. 1, the resin layer 191 is formed on the outer surface of the first coil portion 130a and on the outer surface of the second coil portion 130b. The resin layer 191 may be formed for various purposes. For example, it may be formed for the purpose of enhancing the safety at the time of inserting the guide wire 100 into a blood vessel or the like. For this purpose, the resin layer 191 is preferably hydrophilic. Examples of the hydrophilic material for constituting the resin layer 191 include a cellulose-based polymer material, a polyethylene oxide-based polymer material, a maleic anhydride-based polymer material (for example, a maleic anhydride copolymer such as methyl vinyl ether-maleic anhydride copolymer), an acrylamide-based polymer material (for example, polyacrylamide, block copolymer of polyglycidyl methacrylate-dimethyl acrylamide (PGMA-DMAA)), water-soluble nylon, polyvinyl alcohol, polyvinyl pyrrolidone, or the like. In most cases, those hydrophilic materials exhibit a high lubricating property when wetted (water absorption). Because the distal portion is required to have a high lubricating property, it is preferable to use those hydrophilic materials for the distal portion. The thickness of the resin layer 191 is suitably set depending on the purpose, material, or the like, but the average thickness at wetting is 0.1 to 300 μm, for example.

Furthermore, on the outer surface of the proximal end side of the first core portion 111, the resin layer 192 is formed. The resin layer 192 may be a material capable of reducing friction. Examples of the material capable of reducing friction include polyolefin such as polyethylene, polypropylene or the like, polyvinyl chloride, polyester (PET, PBT, or the like), polyamide, polyimide, polyurethane, polystyrene, polycarbonate, a silicone resin, a fluorine-based resin (PTFE, ETFE, or the like), and composite materials thereof. Furthermore, the resin layer 192 may also include a component other than the material capable of reducing friction (for example, an organic pigment), and it may have the same constitution as the resin layer 194 to be described later, for example. Namely, the resin layer 192 may consist of or be comprised of a first layer which includes a first fluororesin, an organic pigment, and titanium oxide, and a second layer which is formed on the first layer and includes a second fluororesin. By virtue of this composition, the resin layer 192 may be also colored.

As illustrated in FIG. 1, the resin layer 193 is formed on the outer surface of the core portion including the bonding portion 113 of the first core portion 111 and the second core portion 112. The resin layer 193 preferably exhibits a sliding property. Examples of a material for the resin layer 193 include polyolefin such as polyethylene, polypropylene, or the like, polyvinyl chloride, polyester (PET, PBT, or the like), polyamide, polyimide, polyurethane, polystyrene, polycarbonate, a silicone resin, a fluorine-based resin (PTFE, ETFE, or the like), composite materials thereof, or the like.

At least part of the second core portion 112 is coated with the resin layer 194. Namely, the resin layer 194 is a resin layer covering at least the proximal portion of an elongated body (the proximal portion of the core portion 110). To provide a medical device with visibility and identifiability, the resin layer 194 is constituted by or comprised of a first layer (first resin layer) which includes a first fluororesin, an organic pigment, and titanium oxide, and a second layer (second resin layer) which is formed on the first layer and includes a second fluororesin.

The resin layer 194 is preferably formed in a range including a handle part for a doctor. That is, the resin layer 194 is preferably provided on a part of the guide wire 100 (medical device) that includes a part gripped by the doctor during use. The expression "range including a handle part for a doctor" includes, in the case of a guiding catheter having a length that is common for percutaneous transluminal coronary angioplasty (length of 800 to 1000 mm), a portion of the guide wire that is exposed from the catheter proximal end. Specifically, an example includes an embodiment in which the resin layer 194 is formed between a position which is separated by 300 mm from the distal end (i.e., distal-most end) of a guide wire toward the proximal end side and the proximal end of the guide wire. Furthermore, the expression the resin layer 194 "is formed between a position which is separated by 300 mm from the distal end of a guide wire toward the proximal end side and the proximal end of a guide wire" means that the resin layer 194 may be formed over the total length (continuously) of the core portion 110 between the position that is spaced 300 mm from the distal end (i.e., distal-most end) toward the proximal end side and the proximal end of the guide wire, or the resin layer 194 may be formed on a part of the core portion 110 between the position that is spaced 300 mm from the distal end toward the proximal end side and the proximal end of the guide wire. According to the embodiment in which the resin layer 194 is formed on a part of the core portion 110 between a position which is separated by 300 mm from the distal end toward the proximal end side and the proximal end of a guide wire, it is possible to have not only an embodiment in which the resin layer 194 is continuously formed but also an embodiment in which the resin layer 194 is formed at plural separate sites on such part. Thus, the resin layer 194 may extend continuously along the entire axial extent of the core portion 110 from a point spaced 300 mm in the proximal direction from the distal-most end of the guide wire to the proximal end of the core portion 110, or the resin layer 194 may extend along only a part of the axial extent of the core portion 110 from a point spaced 300 mm in the proximal direction from the distal-most end of the guide wire to the proximal end of the core portion 110. In the case of the resin layer 194 extending along only a part of such axial extent of the core portion 110, the resin layer 194 may extend continuously along such part of the axial extent or may extend as plural spaced part segments along such part of the axial extent.

According to an embodiment in which the resin layer 194 "is formed between the position that is separated by 300 mm from the distal end of a guide wire toward the proximal end side and the proximal end of a guide wire", it is preferable that the resin layer 194 is formed between the position that is separated by 300 mm from the distal end (i.e., distal-most end) of a guide wire toward the proximal end side and the position that is separated by 3500 mm from the distal end of the guide wire toward the proximal end side (Embodiment 1). It is more preferable that the resin layer 194 is formed between the position that is separated by 300 mm from the distal end (i.e., distal-most end) of a guide wire toward the proximal end side and the position that is separated by 3000 mm from the distal end of the guide wire toward the proximal end side. It is even more preferable that the resin layer 194 is formed between the position that is separated by 350 mm from the distal end (i.e., distal-most end) of a guide wire toward the proximal end side and the position that is separated by 3000 mm from the distal end (i.e., distal-most end) of the guide wire toward the proximal end side. As the resin layer 194 is formed in the aforementioned range, the guide wire can have a colored range in a handle part used by the doctor to operate the guide wire. Due to this reason, for a procedure involving simultaneous use of plural medical devices, a doctor can rather easily identify each medical device by a handle part even without checking a marker on a proximal end of the guide wire. Furthermore, according to an embodiment in which the resin layer 194 "is formed between the position that is separated by 300 mm from the distal end of a guide wire toward the proximal end side and the proximal end of a guide wire", the resin layer 194 may be formed on the proximal end side of a guide wire. Specifically, the resin layer 194 may be provided at least on a part of the region between the position that is separated by 50 mm from the proximal end (i.e., proximal-most end) of a guide wire toward the distal end side and the proximal end of a guide wire (Embodiment 2). With the resin layer 194 formed in the aforementioned range, easy identification of a guide wire can be achieved at the time of catheter exchange made by a doctor. The guide wire disclosed here may be embody Embodiment 1, may embody Embodiment 2, or may embody both Embodiment 1 and Embodiment 2.

As for the embodiment in which the resin layer 194 is formed on a part of a guide wire between the position that is separated by or spaced 300 mm from the distal end (i.e., distal-most end) of a guide wire toward the proximal end side and the proximal end of a guide wire, when the total length of a guide wire is 1800 mm, for example, (1) the resin layer 194 may be formed at least on a part between the position that is separated by or spaced 400 mm from the distal end (i.e., distal-most end) of a guide wire toward the proximal end side and the position that is separated by or spaced 1500 mm from the distal end (i.e., distal-most end) of a guide wire toward the proximal end side, and/or (2) the resin layer 194 may be formed at least on a part between the position that is separated by or spaced 1750 mm from the distal end or spaced of a guide wire toward the proximal end side and the position that is separated by or spaced 1790 mm from the distal end (i.e., distal-most end) of a guide wire toward the proximal end side. By forming the resin layer 194 on the part (1) above, easier identification of a guide wire by a handle part can be achieved by a doctor, and, by forming the resin layer 194 on the part (2) above, easy identification of a guide wire can be achieved at the time of catheter exchange made by a doctor.

Figure 2:
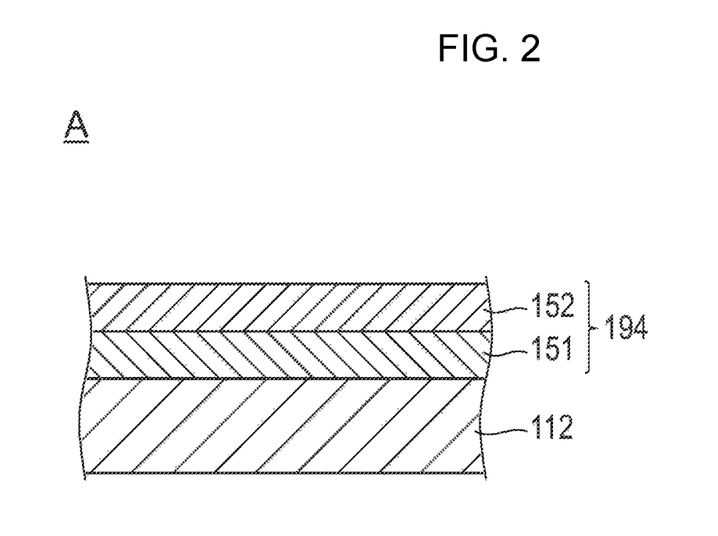
FIG. 2 is an enlarged sectional view of an area [II] surrounded by a one-dot chain line in FIG. 1.

FIG. 2 is an enlarged sectional view of an area [II] surrounded by a one-dot chain line in FIG. 1. In FIG. 2, the resin layer 194 includes a first layer 151 and a second layer 152. In FIG. 2, a second core portion 112, the first layer 151, and the second layer 152 are disposed in this order. Namely, the first layer 151 is disposed as an inner layer (second core portion (elongated body) side) positioned more inwardly than the second layer 152, and the second layer 152 is an outermost layer positioned more outwardly than the first layer 151. The distal-most end of each of first and second resin layers 151, 152 is proximal of the proximal-most end of the tapered portion 111*b* as shown in FIG. 1.

The second layer 152 includes a fluororesin (second fluororesin). The operation for inserting a guide wire involves a part of the proximal end side (proximal side) entering the inside of a catheter. As the second layer 152 includes a fluororesin, frictional resistance on the outer surface of the guide wire is reduced. As a result, frictional resistance (sliding resistance) between the guide wire and the inner wall of the catheter is reduced, and thus the operability of the guide wire inside the catheter is enhanced. In addition, as the second layer 152 includes a fluororesin, kinking (bending) or twisting of a guide wire can be inhibited or prevented when the guide wire is moved/rotated inside the catheter.

Furthermore, with regard to FIG. 1, since the proximal end (proximal-most end) of the guide wire is never introduced into a human body, the proximal end need not exhibit a lubricating property. Thus, considering the manner of use of the guide wire, the proximal end (proximal-most end) is not provided with the resin layer 194. Accordingly, the proximal portion described in the expression that a resin layer "covers at least a proximal portion of an elongated body" is not limited to an embodiment in which the entire proximal end is provided with the resin layer 194, and, it is sufficient that a certain region or a part on the proximal end side of the guide wire is coated with the resin layer.

The total content of the organic pigment and titanium oxide in the second layer 152 is preferably less than 5% by weight (lower limit: 0% by weight), more preferably less than 3% by weight (lower limit: 0% by weight), even more preferably less than 1% by weight (lower limit: 0% by weight), and most preferably 0% by weight relative to the solid content of the second layer. As the total content of the organic pigment and titanium oxide in the second layer is low, not only the surface smoothness of the second layer as an outermost layer is enhanced but also peeling of the second layer can be suppressed. Furthermore, the content of particles other than the organic pigment and titanium oxide that are included in the second layer (for example, inorganic pigment or organic pigment other than them) is also preferably less than 5% by weight (lower limit: 0% by weight), more preferably less than 3% by weight (lower limit: 0% by weight), even more preferably less than 1% by weight (lower limit: 0% by weight), and most preferably 0% by weight. Furthermore, the solid content means a component excluding a solvent which evaporates at the time of drying or baking a coating solution, and a fluororesin, an organic pigment, titanium oxide, a dispersant, a thickening agent, or the like correspond to the solid content.

The second layer including a fluororesin to provide the sliding property has a very low adhesion property to an elongated body such as a core member or the like. To enhance the adhesion property between the second layer and an elongated body, the first layer is provided between an elongated body and the second layer. That is, the first layer is formed on or overlies an elongated body, and the second layer is formed on or overlies the first layer.

The expression "the second layer is formed on the first layer" indicates that an elongated body, the first layer, and the second layer are formed or arranged in this order, and it does not necessarily indicate an embodiment in which the second layer and the first layer are directly adjacent to each other. It is also possible that an intermediate layer is included between the first layer and the second layer. Similarly, it is not necessary that the first layer and an elongated body are directly adjacent to each other, and it is possible that an intermediate layer is included between an elongated body and the first layer. However, for increasing the adhesion property of the second layer to the elongated body, it is preferable that the elongated body and the first layer are directly adjacent to each other and also the first layer and the second layer are directly adjacent to each other as illustrated in FIG. 2.

The first layer may be either a single layer or a multi-layer, and the second layer may be either a single layer or a multi-layer.

[Resin Layer]

The resin layer 194 includes the first layer 151 which includes a first fluororesin, an organic pigment, and titanium oxide, and the second layer 152 which is formed on the first layer and includes a second fluororesin.

The thickness of the resin layer 194 is not particularly limited. However, from the viewpoint of imparting sliding properties or from the viewpoint of imparting visibility or identifiability, the thickness of the resin layer 194 is preferably 1 µm or more, more preferably 2 µm or more, and even more preferably 3 µm or more. Furthermore, in consideration of the adhesion properties of the coating or the influence on physical properties of the guide wire, the thickness of the resin layer 194 is preferably 200 µm or less, more preferably 100 µm or less, and even more preferably 50 µm or less. Specifically, the thickness of the resin layer 194 is preferably 1 to 200 µm, and more preferably 3 to 50 µm.

[First and Second Fluororesins]

The first layer 151 includes the first fluororesin and the second layer 152 includes the second fluororesin.

The first fluororesin and the second fluororesin are not particularly limited, but, from the viewpoint of imparting sliding property to the surface, chemical resistance, anti-thrombogenicity, non-sticking property, or the like, they preferably contain at least one selected from the group consisting of polytetrafluoroethylene (PTFE), tetrafluoroethylene-perfluoroalkyl vinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE). They more preferably contain at least one of polytetrafluoroethylene (PTFE) and tetrafluoroethylene-hexafluoropropylene copolymer (FEP). From the viewpoint of melting the first layer and the second layer at even lower temperatures, it is particularly preferable for the first fluororesin to contain both polytetrafluoroethylene (PTFE) and tetrafluoroethylene-hexafluoropropylene copolymer (FEP). In that case, the weight ratio between PTFE and FEP (PTFE:FEP) is preferably 1:0.1 to 1:15, more preferably 1:1 to 1:10, and even more preferably 1:1 to 1:7. Furthermore, it is particularly preferable that the second fluororesin is polytetrafluoroethylene (PTFE).

The first fluororesin and the second fluororesin may be the same type or a different type. Furthermore, it is also possible that each of the first fluororesin and the second fluororesin contains plural kinds of a fluororesin.

[Organic Pigment]

In the medical device disclosed by way of example here, the organic pigment has a role of coloring the first layer and providing the visibility and identifiability to a medical device. As for the organic pigment, from the viewpoint of the visibility on non-woven fabric having a color such as green, blue, or the like and identifiability from other medical devices having colors such as green, blue, or the like, it is preferable to use an organic pigment representing a color such as red, yellow, orange, or the like.

Examples of the organic pigment representing a color such as red, yellow, orange, or the like include a water insoluble azo-based pigment such as toluidine red, toluidine maroon, hanza yellow, benzidine yellow, pyrazolone red, or the like; a water soluble azo-based pigment such as lithol red, helio bordeaux, pigment scarlet, permanent red 2B, or the like; an anthraquinone-based pigment such as dianthraquinonyl red or the like; a quinacridone-based pigment such as quinacridone red, quinacridone magenta, or the like; a pyranthrone-based pigment such as pyranthrone red, pyranthrone orange, or the like; a perylene-based pigment such as perylene red, perylene scarlet, or the like; a diketopyrrolopyrrole-based pigment such as diketopyrrolopyrrole red or the like; and the like. Namely, according to one embodiment of the medical device, the organic pigment includes at least one selected from the group consisting of an azo-based pigment, an anthraquinone-based pigment, a quinacridone-based pigment, a pyranthrone-based pigment, a perylene-based pigment, and a diketopyrrolopyrrole-based pigment. Among them, it is preferable that the organic pigment includes a quinacridone-based pigment.

When the organic pigment is exemplified with a color index (C. I.) number, C.I. Pigment Yellow 12, C.I. Pigment Yellow 13, C.I. Pigment Yellow 14, C.I. Pigment Yellow 17, C.I. Pigment Yellow 20, C.I. Pigment Yellow 24, C.I. Pigment Yellow 74, C.I. Pigment Yellow 83, C.I. Pigment Yellow 86, C.I. Pigment Yellow 93, C.I. Pigment Yellow 109, C.I. Pigment Yellow 110, C.I. Pigment Yellow 117, C.I. Pigment Yellow 120, C.I. Pigment Yellow 125, C.I. Pigment Yellow 128, C.I. Pigment Yellow 129, C.I. Pigment Yellow 137, C.I. Pigment Yellow 138, C.I. Pigment Yellow 139, C.I. Pigment Yellow 147, C.I. Pigment Yellow 148, C.I. Pigment Yellow 150, C.I. Pigment Yellow 151, C.I. Pigment Yellow 153, C.I. Pigment Yellow 154, C.I. Pigment Yellow 155, C.I. Pigment Yellow 166, C.I. Pigment Yellow 168, C.I. Pigment Yellow 180, C.I. Pigment Yellow 185; C.I. Pigment Orange 16, C.I. Pigment Orange 36, C.I. Pigment Orange 43, C.I. Pigment Orange 51, C.I. Pigment Orange 55, C.I. Pigment Orange 59, C.I. Pigment Orange 61; C.I. Pigment Red 9, C.I. Pigment Red 48, C.I. Pigment Red 49, C.I. Pigment Red 52, C.I. Pigment Red 53, C.I. Pigment Red 57, C.I. Pigment Red 97, C.I. Pigment Red 122, C.I. Pigment Red 123, C.I. Pigment Red 149, C.I. Pigment Red 168, C.I. Pigment Red 177, C.I. Pigment Red 180, C.I. Pigment Red 192, C.I. Pigment Red 202, C.I. Pigment Red 206, C.I. Pigment Red 215, C.I. Pigment Red 216, C.I. Pigment Red 217, C.I. Pigment Red 220, C.I. Pigment Red 223, C.I. Pigment Red 224, C.I. Pigment Red 226, C.I. Pigment Red 227, C.I. Pigment Red 228, C.I. Pigment Red 238, C.I. Pigment Red 240; C.I. Pigment Violet 19, C.I. Pigment Violet 23, C.I. Pigment Violet 29, C.I. Pigment Violet 30, C.I. Pigment Violet 37, C.I. Pigment Violet 40, C.I. Pigment Violet 50, or the like can be mentioned. They may be used either singly, or two or more kinds thereof may be used in combination.

The content of the organic pigment in the first layer is, relative to the content of the first fluororesin, preferably 5% by weight or more, more preferably 20% by weight or more, even more preferably 30% by weight or more, and particularly preferably 35% by weight or more. With the content within this range, the color-exhibition property of the first layer becomes favorable, and thus the visibility or identifiability of a medical device provided with the resin layer is enhanced. Furthermore, from the viewpoint of the dispersion property of the organic pigment in the first layer or the adhesion property of a coating, the content of the organic pigment in the first layer is, relative to the content of the first fluororesin, preferably 300% by weight or less, more preferably 250% by weight or less, even more preferably 200% by weight or less, and particularly preferably 150% by weight or less. In particular, from the viewpoint of even further enhancement of the identifiability of a medical device or the adhesion property of a coating, the content of the organic pigment relative to the content of the first fluororesin in the first layer is preferably 100% by weight or less, and more preferably 95% by weight or less. Furthermore, for the same reason, the content of the organic pigment is, relative to the solid content of the first layer, preferably 1 to 150% by weight, more preferably 3 to 100% by weight, even more preferably 5 to 50% by weight, and particularly preferably 8 to 40% by weight. In particular, from the viewpoint of even further enhancement of the identifiability of a medical device or the adhesion property of a coating, the content of the organic pigment relative to the content of the first fluororesin in the first layer is preferably 8 to 35% by weight, more preferably 8 to 30% by weight, and particularly preferably 8 to 25% by weight.

From the viewpoint of the dispersion property and coloration property, the average particle diameter of the organic pigment is preferably 50 to 900 nm, and more preferably 90 to 600 nm. The average particle diameter of the organic pigment indicates a median diameter based on volume that is measured by laser diffraction scattering method.

To ensure the dispersion stability, the organic pigment may be surface-treated by a known technique such as acidic treatment or basic treatment, treatment with a synergist or various coupling agents, or the like.

Only one kind of the organic pigment may be used, or two or more kinds of the organic pigment may be used in combination.

[Titanium Oxide]

In the medical device disclosed here by way of example, the titanium oxide has a role of increasing the color-exhibition property and strength of the first layer. The titanium oxide may be any one of a rutile type and an anatase type. However, in terms of the color-exhibition property, a rutile type titanium oxide is preferable.

From the viewpoint of the dispersion property or dispersion stability, the average particle diameter of the titanium oxide is preferably 50 to 700 nm, more preferably 100 to 500 nm, and even more preferably 200 to 300 nm. The average particle diameter of titanium oxide indicates a median diameter based on volume that is measured by laser diffraction scattering method.

The content of the titanium oxide in the first layer is preferably 5% by weight or more relative to the content of the first fluororesin, more preferably 20% by weight or more relative to the content of the first fluororesin, even more preferably 30% by weight or more relative to the content of the first fluororesin, and particularly preferably 40% by weight or more relative to the content of the first fluororesin, 50% by weight or more relative to the content of the first fluororesin, 60% by weight or more relative to the content of the first fluororesin, 70% by weight or more relative to the content of the first fluororesin, 80% by weight relative to the content of the first fluororesin, 90% by weight or more relative to the content of the first fluororesin. When the content is within the above range, the color-exhibition property of the first layer becomes favorable, and thus the identifiability is enhanced. Furthermore, a medical device having an excellent adhesion property between the first layer and the second layer and excellent strength can be obtained. Furthermore, for the same reason, the content of the titanium oxide in the first layer is preferably 400% by weight or less relative to the content of the first fluororesin, and more preferably 360% by weight or less relative to the content of the first fluororesin. Furthermore, for the same reason, the content of the titanium oxide is preferably 1 to 150% by weight relative to the solid content of the first layer, more preferably 3 to 100% by weight relative to the solid content of the first layer, even more preferably 5 to 50% by weight relative to the solid content of the first layer, and particularly preferably 8 to 40% by weight relative to the solid content of the first layer.

The content of the titanium oxide in the first layer is preferably 10% by weight or more relative to 100% by weight of the content of the organic pigment, more preferably 25% by weight or more relative to 100% by weight of the content of the organic pigment, even more preferably 50% by weight or more relative to 100% by weight of the content of the organic pigment, 60% by weight or more, 70% by weight or more, 80% by weight or more, 90% by weight or more, and particularly preferably 100% by weight or more relative to 100% by weight of the content of the organic pigment. As the content is within the above range, the color-exhibition property of the first layer becomes favorable, and thus the identifiability is enhanced. Furthermore, the adhesion property between the first layer and the second layer and the strength become favorable. Furthermore, from the viewpoint of increasing the brightness of a coating color and further enhancing the visibility and identifiability of a medical device, the content of the titanium oxide in the first layer is more preferably 110% by weight or more relative to 100% by weight of the content of the organic pigment, 120% by weight or more relative to 100% by weight of the content of the organic pigment, 130% by weight or more relative to 100% by weight of the content of the organic pigment, 140% by weight or more relative to 100% by weight of the content of the organic pigment, and particularly preferably 150% by weight or more relative to 100% by weight of the content of the organic pigment, 160% by weight or more relative to 100% by weight of the content of the organic pigment, 170% by weight or more relative to 100% by weight of the content of the organic pigment, 180% by weight or more relative to 100% by weight of the content of the organic pigment, 185% by weight or more relative to 100% by weight of the content of the organic pigment. Furthermore, the content of the titanium oxide in the first layer is, when the color-exhibition property of a medical device is considered, preferably 600% by weight or less relative to 100% by weight of the content of the organic pigment, more preferably 550% by weight or less relative to 100% by weight of the content of the organic pigment, even more preferably 500% by weight or less relative to 100% by weight of the content of the organic pigment, and particularly preferably 400% by weight or less, relative to 100% by weight of the content of the organic pigment. Namely, in one embodiment of the medical device representing an example of the inventive medical device, the content of the titanium oxide relative to 100% by weight of the content of the organic pigment is preferably 25% by weight or more and 600% by weight or less, and more preferably 100% by weight or more and 400% by weight or less.

[Dispersant]

In the medical device disclosed here by way of example, the first layer may additionally include a dispersant. By including a dispersant, the dispersion property of titanium oxide in an organic pigment or a fluororesin is enhanced, and the color-exhibition property or strength of the first layer is further enhanced.

According to one embodiment, the first layer additionally includes a dispersant, and the content of the dispersant is 80% by weight or less relative to 100% by weight of the total content of the organic pigment and titanium oxide. In particular, from the viewpoint of the adhesion property between the first layer and the second layer, the content of the dispersant is, relative to 100% by weight of the total content of the organic pigment and titanium oxide, preferably 70% by weight or less, 60% by weight or less, 50% by weight or less, 40% by weight or less, 30% by weight, more preferably 25% by weight or less, more preferably 20% by weight or less, even more preferably 15% by weight or less, and particularly preferably 12% by weight or less. Meanwhile, from the viewpoint of further enhancing the color-exhibition property or strength of the first layer, the content of the dispersant is, relative to 100% by weight of the total content of the organic pigment and titanium oxide, preferably 1% by weight or more, more preferably 2% by weight or more, even more preferably 3% by weight or more, and particularly preferably 3.5% by weight or more. Furthermore, for the same reason, the content of the dispersant is preferably 0.5 to 30% by weight relative to the solid content of the first layer, more preferably 0.5 to 25% by weight relative to the solid content of the first layer, even more preferably 0.5 to 20% by weight relative to the solid content of the first layer, still even more preferably 1 to 15% by weight relative to the solid content of the first layer, and particularly preferably 1.5 to 12% by weight relative to the solid content of the first layer. The blending ratio of the dispersant is obtained to the third decimal digit, and a value obtained by rounding to the second decimal digit is employed.

The dispersant is preferably a polymer dispersant. The polymer dispersant suppresses aggregation among organic pigments or titanium oxides by steric hindrance of a main chain or a side chain, resulting in enhancement of the dispersion property and stabilization of organic pigment or titanium oxide. The weight average molecular weight of a polymer constituting the dispersant is preferably 500 to 200,000. Herein, the weight average molecular weight of a polymer constituting the dispersant indicates the polystyrene-converted weight average molecular weight that is measured by gel permeation chromatography (solvent for development: tetrahydrofuran).

As for the dispersant, a commercially available product may be used. Examples of the dispersant which may be used include DISPERBYK-2000, DISPERBYK-2013, and DISPERBYK-2055 (manufactured by BYK-Chemie), DISPARLON DA-703-50 (manufactured by Kusumoto Chemicals, Ltd.), AJISPER-PB821, AJISPER-PB822, and AJISPER-PB881 (manufactured by Ajinomoto Fine-Techno Co., Inc.), or the like.

Only one kind of the dispersant may be used, or two or more kinds of dispersant may be used in combination.

[Thickening Agent]

Furthermore, to further enhance the dispersion stability of the organic pigment and titanium oxide or to control the coating thickness by adjusting the viscosity of a coating solution for forming the first layer, it is preferable for the first layer to further contain a thickening agent. Examples of the thickening agent include polyamide-based wax, metal soaps, organic clay mineral, polyethylene oxide-based compound, hydrogenated castor oil wax, and inorganic fine particles such as fine powder of silicon dioxide, or the like. From the viewpoint of further enhancing the stability of a coating solution, the thickening agent is more preferably metal soaps, organic clay mineral, polyethylene oxide-based compound, or inorganic fine particles such as fine powder of silicon dioxide or the like. From the viewpoint that the dispersion property of the titanium oxide is further stabilized, organic clay mineral is more preferable.

Examples of the organic clay mineral include a material obtained by performing organic treatment of a clay mineral such as natural mineral montmorillonite (bentonite), hectorite, saponite that are classified into smectites, layered clay mineral, chain-like clay mineral such as sepiolite or the like, and also long-fiber shape clay mineral such as palygorskite or the like. The organic treatment is generally performed by using an alkyl quaternary ammonium compound, and, according to hydrophobization of a surface of clay mineral, the dispersion property of obtained organic clay mineral is enhanced.

As for the thickening agent, a commercially available product may be used. Examples of the thickening agent which may be used include BENTONE LT, BENAQUA 4000 (manufactured by Elementis Specialties), Optigel CK, Optigel LX, GARAMITE 7305 (manufactured by BYK-Chemie), KUNIBIS (registered trademark)-110, SUMECTON (registered trademark)-SA, SUMECTON (registered trademark)-SAN, SUMECTON (registered trademark)-STN (manufactured by KUNIMINE INDUSTRIES CO., LTD.), S-BEN (registered trademark) N400, S-BEN (registered trademark) NX, S-BEN (registered trademark) NZ (manufactured by HOJUN Co., Ltd.), or the like.

Blending amount of the thickening agent is suitably set in consideration of the blending amount of the organic pigment and titanium oxide, dispersant to be used, or the like. From the viewpoint of the stability of a coating solution, the thickening agent is preferably 0.01 to 10% by weight, more preferably 0.10 to 5.00% by weight, and even more preferably 0.20 to 2.00% by weight, relative to the solid content of the first layer. Furthermore, the blending ratio of the thickening agent is obtained to the third decimal digit, and a value obtained by rounding to the second decimal digit is employed.

Only one kind of the thickening agent may be used, or two or more kinds of thickening agents may be used in combination.

The first layer may also include a binder resin for the purpose of enhancing the adhesion property to an elongated body. The binder resin is not particularly limited, and examples thereof include a polyamideimide resin, an epoxy resin, a polyphenylene sulfide resin, a polyether sulfone resin, a polyether ketone resin, a polyether amide resin, a polysulfone resin, a polyimide resin, a parylene resin, or the like. Only one kind of the binder resin may be used, or two or more kinds of binder resins may be used in combination.

The content of the binder resin in the first layer is, in consideration of the adhesion property to an elongated body, preferably 5 to 50% by weight relative to the solid content of the first layer, and more preferably 10 to 40% by weight relative to the solid content of the first layer.

The first layer may include particles other than titanium oxide (for example, pigment for coloration). However, if the content of the particles is excessively high, the first layer becomes brittle, yielding an insufficient effect of enhancing the adhesion property of the second layer to an elongated body. Due to this reason, the content of the particles other than titanium oxide is preferably 10% by weight or less (lower limit: 0% by weight), and more preferably 5% by weight or less (lower limit: 0% by weight).

The content of the first fluororesin in the first layer is, in consideration of the adhesion property to the second layer, preferably 5 to 50% by weight relative to the solid content of the first layer, and more preferably 10 to 40% by weight relative to the solid content of the first layer.

The thickness of the first layer is, although not particularly limited, from the viewpoint of the visibility and identifiability of a medical device, preferably 0.8 µm or more, more preferably 1 µm or more, and even more preferably 2 µm or more. Furthermore, the thickness of the first layer is, in consideration of the adhesion property between the first layer and a layer adjacent to the first layer (for example, elongated body, the second layer, an intermediate layer which is adjacent to the first layer, or the like), preferably 100 μm or less, more preferably 50 μm or less, even more preferably 25 μm or less, and particularly preferably 10 μm or less. Furthermore, the thickness of the first layer is preferably 0.8 to 100 μm, more preferably 1 to 50 μm, even more preferably 1 to 25 μm, and particularly preferably 2 to 10 μm.

The content of the second fluororesin in the second layer is, in consideration of the effect of exhibiting the sliding property of the outer surface of a medical device, preferably 75 to 100% by weight, and more preferably 85 to 100% by weight.

The thickness of the second layer is, although not particularly limited, in consideration of providing the sliding property to a medical device and suppressing discoloration of the first layer caused by baking, preferably 0.8 μm or more, more preferably 1 μm or more, and even more preferably 2 μm or more. Furthermore, in consideration of the adhesion property between the second layer and a layer adjacent to the second layer (for example, the first layer, an intermediate layer which is adjacent to the second layer, or the like), the thickness of the second layer is preferably 50 μm or less, more preferably 25 μm or less, and even more preferably 10 μm or less.

Furthermore, the thickness of a layer described in the present specification indicates an average thickness value which is obtained from the thickness of 5 points that are arbitrarily selected from a part in which the subject layer is present. Furthermore, the thickness of each layer can be measured from a cross-sectional image of a medical device. Specifically, after taking a cross-sectional image of a medical device, by taking the half of the value that is obtained by subtracting the outer diameter of an elongated body from the outer diameter of a medical device, the thickness of a layer can be calculated. In that case, the thickness is obtained to the second decimal digit, and a value obtained by rounding the second decimal digit to the first decimal digit is employed as a mean value. The thickness of the first layer can be calculated by subtracting the thickness of the second layer from the total thickness of a resin layer.

Other additives may also be added to each layer constituting the resin layer, if necessary. Examples of the additives include an organic pigment, an inorganic pigment, a dispersion stabilizer, a leveling agent, an anti-foaming agent, a chelating agent, an anti-oxidant, a plasticizer, or the like.

[Method for Production]

The method for producing the medical device of the present embodiment, though not particularly limited, may preferably be a production method including coating a coating solution including the first fluororesin, the organic pigment and the titanium oxide (hereinbelow, referred to as a coating solution for forming the first layer) at least on a proximal portion of the elongated body to form a first coating film, coating a coating solution including a second fluororesin (hereinbelow, referred to as a coating solution for forming the second layer) on the first coating film to form a second coating film, and then carrying out baking at a temperature which is equal to or higher than the melting points of the first fluororesin and the second fluororesin.

First, the coating solution for forming the first layer is prepared. The coating solution for forming the first layer includes the first fluororesin, the organic pigment, the titanium oxide, the binder resin, and the dispersant. The coating solution preferably includes a solvent, which is a dispersion medium for dispersing them. As for the solvent, water, an organic solvent, and a mixture solvent of water and organic solvent can be used.

As for the organic solvent, an aromatic solvent such as toluene, xylene or the like, a ketone-based solvent such as acetone, methyl ethyl ketone, methyl isobutyl ketone, cyclohexanone or the like, and a cellosolve-based organic solvent such as methyl cellosolve, ethyl cellosolve, or the like can be used. Only one kind of the organic solvent may be used, or two or more kinds of organic solvents may be used in combination.

The added amount of the organic solvent is suitably set in consideration of the viscosity of the coating solution and dispersion property of each component. However, preferably, the organic solvent is added such that it is present at 40 to 70% by weight in the coating solution for forming the first layer.

The order of mixing the organic solvent with each component is not particularly limited, and it may be any addition order like mixing in bulk the organic solvent and each component or adding each component in turn to the organic solvent, or the like.

The method for coating the coating solution for forming the first layer on a proximal portion of the elongated body is not particularly limited. Specifically, dipping (immersing), dripping, a doctor blade, spin coating, brush coating, spray coating, a roll coater, air knife coating, curtain coating, wire bar coating, gravure coating, screen printing, or the like can be mentioned. From the viewpoint of having an even coating on the surface and easily controlling the film thickness, dipping (immersing) is preferably used as the method for coating the coating solution for forming the first layer. The pulling-up speed for dipping is suitably set so as to have a desired film thickness. An example of a pulling-up speed is 5 to 150 mm/second. Furthermore, the viscosity of the coating solution is suitably set so as to have a desired film thickness. An example of the viscosity of the coating solution is 5 to 70 Pa s (25° C.).

It is preferable that, after the coating solution for forming the first layer is coated at least on the proximal portion of the elongated body, the coating solution for forming the first layer is dried. The drying temperature is not particularly limited as long as it allows removal of a solvent. However, it is preferably 50 to 300° C., and more preferably 100 to 200° C. The drying time is not particularly limited, either, as long as it allows removal of a solvent. However, it is preferably 10 minutes or shorter, more preferably 5 minutes or shorter, and even more preferably 60 seconds or shorter.

Furthermore, it is also possible that the steps of coating and drying are repeated.

The first coating film is obtained as described above.

Subsequently, the coating solution for forming the second layer is prepared. The coating solution for forming the second layer includes the second fluororesin. The coating solution preferably includes a solvent, which is a dispersion medium for dispersing the second fluororesin. As for the solvent, water, an organic solvent, and a mixture solvent of water and organic solvent can be used. As for the organic solvent, an organic solvent used for the above coating solution for forming the first layer can be mentioned.

Prepared coating solution for forming the second layer is coated on the first coating film. The method for coating the coating solution for forming the second layer on the first coating film is not particularly limited. Specifically, dipping (immersing), dripping, a doctor blade, spin coating, brush coating, spray coating, a roll coater, air knife coating, curtain coating, wire bar coating, gravure coating, screen printing, or the like can be mentioned. From the viewpoint of having an even coating on a surface and easily controlling the film thickness, dipping (immersing) is preferably used as the method for coating the coating solution for forming the second layer. The pulling-up speed for dipping is suitably set so as to have a desired film thickness. An example of a pulling-up speed is 5 to 150 mm/second. Furthermore, the viscosity of the coating solution is suitably set so as to have a desired film thickness. An example of the viscosity of the coating solution is 5 to 70 Pa s (25° C.).

It is preferable that, after the coating solution for forming the second layer is coated on the first coating film, the coating solution for forming the second layer is dried. The drying temperature is not particularly limited as long as it allows removal of a solvent. However, it is preferably 50 to 300° C., and more preferably 100 to 200° C. The drying time is not particularly limited, either, as long as it allows removal of a solvent. However, it is preferably 10 minutes or shorter, more preferably 5 minutes or shorter, and even more preferably 60 seconds or shorter.

The second coating film is obtained as described above.

Finally, baking is carried out at a temperature which is equal to or higher than the melting points of the first fluororesin and the second fluororesin. By carrying out the baking at a temperature which is equal to or higher than the melting points, the fluororesins are melted to form a coating.

The baking temperature is not particularly limited as long as it is equal to or higher than melting points of the first fluororesin and the second fluororesin, but it is preferably higher by 20° C. or more than the higher one of the melting points of the first fluororesin and the second fluororesin (i.e., the baking temperature preferably exceeds, by at least 20° C., the greater of the melting point of the first fluororesin and the melting point of the second fluororesin). The baking temperature is preferably 300 to 550° C., and more preferably 400 to 550° C. The baking time is preferably 30 seconds or longer. As it is 30 seconds or longer, baking of the fluororesins is suitably carried out, and thus enhanced adhesion property and strength are yielded. The upper limit of the baking time is, although not particularly limited, from the viewpoint of the production efficiency and reducing the coloration (yellowness), preferably 2 minutes or shorter, and more preferably 60 seconds or shorter.

EXAMPLES

Hereinbelow, the effect of the medical device disclosed here is described using the following Examples and Comparative Examples. In Examples, descriptions like "parts" and "%" are used, and, unless specifically described otherwise, they represent "parts by weight" and "% by weight", respectively. Furthermore, unless specifically described otherwise, each operation is carried out at room temperature (25° C.).

Example 1

[Preparation of Coating Solution for Forming the First Layer]

32.0 g of a quinacridone-based organic pigment (C.I. Pigment Violet 19, average particle diameter of 430 nm) (relative to the solid content: 36.8% by weight), 8.0 g of titanium oxide (C.I. Pigment White 6, rutile type, average particle diameter of 250 nm) (relative to the organic pigment: 25% by weight, relative to the solid content: 9.2% by weight), 132.0 g of methyl isobutyl ketone as a solvent, 5.4 g of polytetrafluoroethylene (PTFE, average particle diameter of 0.20 μm, melting point of 327° C.), 16.1 g of tetrafluoroethylene-hexafluoropropylene copolymer (FEP, average particle diameter of 0.20 μm, melting point of 270° C.), 21.5 g of polyphenylene sulfide resin as a binder resin, 3.2 g of DISPERBYK 2055 (manufactured by BYK-Chemie) as a dispersant (relative to the organic pigment and the titanium oxide: 8% by weight, relative to the solid content: 3.7% by weight), and 0.8 g of GARAMITE 7305 as a thickening agent (manufactured by BYK-Chemie) (relative to the solid content: 0.9% by weight) were admixed with one another and stirred using a ball mill to prepare a coating solution for forming the first layer.

[Preparation of Coating Solution for Forming the Second Layer]

By mixing 100.0 g of polytetrafluoroethylene (PTFE, average particle diameter of 0.20 μm, melting point of 327° C.) with 100.0 g of water, a coating solution for forming the second layer was prepared.

[Coating]

A metal element wire (SUS302, outer diameter of 0.340 mm) was immersed in the coating solution for forming the first layer, and pulled up at 14 mm/second. After that, it was dried for 60 seconds at 200° C. by using a heater. Subsequently, the metal element wire coated with the first layer was immersed in the coating solution for forming the second layer, and pulled up at 20 mm/second. After that, the metal element wire coated with the first and second layers was dried for 60 seconds at 200° C. using a heater. Finally, the metal element wire coated with the first and second layers was baked for 60 seconds at 500° C. to obtain a guide wire.

The thickness of the first layer of the obtained guide wire was 2.0 μm, the thickness of the second layer was 3.0 μm, and thickness of the resin layer (the first layer+ the second layer) was 5.0 μm.

Example 2

A guide wire was obtained in the same manner as Example 1 except that, for preparing a coating solution for forming the first layer, the blending amount of the quinacridone-based organic pigment is changed to 20.0 g (relative to the solid content: 23.0% by weight) and the blending amount of the titanium oxide is changed to 20.0 g (relative to the organic pigment: 100% by weight, relative to the solid content: 23.0% by weight).

Example 3

A guide wire was obtained in the same manner as Example 1 except that, for preparing a coating solution for forming the first layer, the blending amount of the quinacridone-based organic pigment is changed to 16.0 g (relative to the solid content: 18.4% by weight) and the blending amount of the titanium oxide is changed to 24.0 g (relative to the organic pigment: 150% by weight, relative to the solid content: 27.6% by weight).

Example 4

A guide wire was obtained in the same manner as Example 1 except that, for preparing a coating solution for forming the first layer, the blending amount of the quinacridone-based organic pigment is changed to 14.0 g (relative to the solid content: 16.1% by weight) and the blending amount of the titanium oxide is changed to 26.0 g (relative to the organic pigment: 186% by weight, relative to the solid content: 29.9% by weight).

Example 5

A guide wire was obtained in the same manner as Example 1 except that, for preparing a coating solution for forming the first layer, the blending amount of the quinacridone-based organic pigment is changed to 8.0 g (relative to the solid content: 9.2% by weight) and the blending amount of the titanium oxide is changed to 32.0 g (relative to the organic pigment: 400% by weight, relative to the solid content: 36.8% by weight).

Comparative Example 1

A guide wire was obtained in the same manner as Example 1 except that, for preparing a coating solution for forming the first layer, the titanium oxide is not blended.

Comparative Example 2

A guide wire was obtained in the same manner as Example 5 except that, for preparing a coating solution for forming the first layer, the quinacridone-based organic pigment is not blended.

For the guide wires obtained from Examples 1 to 5 and Comparative Examples 1 and 2, visibility on a drape, identifiability (distinguishability) from a guide wire with another color, and peeling resistance of a coating were evaluated according to the following methods. The results are shown in the following Table 1.

[Evaluation Method: Visibility]

On a blue drape for operation (trade name: Solution Pack, manufactured by Terumo Corporation), the guide wires obtained from Examples and Comparative Examples were arranged, and visibility of the guide wires on the drape was determined.

◯: The guide wire can be visually recognized on a drape.

X: The guide wire is difficult to visually recognize or identify on a drape.

[Evaluation Method: Identifiability from Other Color Guide Wires]

On a blue drape for operation (trade name: Solution Pack, manufactured by Terumo Corporation), the guide wires obtained from the Examples and Comparative Examples, and a blue guide wire (trade name: Runthrough NS, manufactured by Terumo Corporation), a green guide wire (trade name: Hi-TORQUE BALANCE MIDDLEWEIGHT, manufactured by Abbott) and a white guide wire (trade name: PT2, manufactured by Boston Scientific Corporation) were arranged, and identifiability (distinguishability) of the obtained guide wires from the blue green and white guide wires was visually determined.

⊙: The evaluated guide wire can be clearly identified from the blue, green and white guide wires.

◯: The evaluated guide wire can be identified from the blue, green and white guide wires.

X: The evaluated guide wire is difficult to identify or distinguish from the blue, green and white guide wires.

[Evaluation Method: Peeling Resistance]

The guide wires obtained from Examples 1 to 5 and Comparative Examples 1 and 2 were tightened with a torque device (RADIFOCUS Torque Device, manufactured by Terumo Corporation) at condition of 10 N·cm, and, in a state in which the guide wire is fixed, the torque device was rotated 10 times. After that, the presence or absence of peeling of the coating (peeling resistance) was determined.

⊙: Peeling is not visually observed (no change with a microscope).

◯: Peeling is not visually observed (blemishes are observed with a microscope).

X: Peeling is visually observed.

When the peeling resistance is either "⊙" or "◯", it can be said that the coating has an excellent adhesion property (adhesion property between the first layer and the second layer, and adhesion property between the first layer and the elongated body), and also has favorable strength.

TABLE 1

|  | Comparative Example 1 | Example 1 | Example 2 | Example 3 | Example 4 | Example 5 | Comparative Example 2 |
|---|---|---|---|---|---|---|---|
| Titanium oxide:Organic pigment (weight ratio) | 0:100 | 20:80 | 50:50 | 60:40 | 65:35 | 80:20 | 100:0 |
| Titanium oxide (relative to organic pigment, % by weight) | 0 | 25 | 100 | 150 | 186 | 400 | — |
| Organic pigment (relative to first fluororesin, % by weight) | 148.8 | 148.8 | 93.0 | 74.4 | 65.1 | 37.2 | 0 |
| Visibility | ◯ | ◯ | ◯ | ◯ | ◯ | ◯ | ◯ |
| Identifiability | X | ◯ | ⊙ | ⊙ | ⊙ | ⊙ | X |
| Peeling resistance | X | ◯ | ⊙ | ⊙ | ⊙ | ⊙ | ⊙ |

As shown in Table 1, the guide wires having a coating in which the organic pigment and the titanium oxide are used in combination (Examples 1 to 5) have high visibility on a blue non-woven fabric (drape) and excellent identifiability from the guide wires with other color (blue, green and white), and they also have excellent adhesion property and strength of the coating. Furthermore, when the content of the titanium oxide is prepared to be the same or higher than the content of the organic pigment, the adhesion property and strength of the coating were further enhanced.

On the other hand, the guide wires having a coating in which the organic pigment and the titanium oxide are not used in combination (Comparative Examples 1 and 2) show a result indicating poor identifiability from the guide wires with other color (blue, green and white). Furthermore, according to Comparative Example 1, as the coating in which the titanium oxide is not used has low peeling resistance, it is considered that at least one of the adhesion property and strength is insufficient.

Example 6

A guide wire was obtained in the same manner as Example 4 except that, for preparing a coating solution for forming the first layer, the addition amount of DISPERBYK-2055 as a dispersant is set at 1.5 g (relative to the organic pigment and the titanium oxide: 3.8% by weight, relative to the solid content: 1.8% by weight).

Example 7

A guide wire was obtained in the same manner as Example 4 except that, for preparing a coating solution for forming the first layer, the addition amount of DISPERBYK-2055 as a dispersant is set at 1.9 g (relative to the organic pigment and the titanium oxide: 4.8% by weight, relative to the solid content: 2.2% by weight).

Example 8

A guide wire was obtained in the same manner as Example 4 except that, for preparing a coating solution for forming the first layer, the addition amount of DISPERBYK-2055 as a dispersant is set at 4.8 g (relative to the organic pigment and the titanium oxide: 12.0% by weight, relative to the solid content: 5.4% by weight).

Example 9

A guide wire was obtained in the same manner as Example 4 except that, for preparing a coating solution for forming the first layer, the addition amount of DISPERBYK-2055 as a dispersant is set at 10.0 g (relative to the organic pigment and the titanium oxide: 25.0% by weight, relative to the solid content: 10.7% by weight).

Example 10

A guide wire was obtained in the same manner as Example 4 except that, for preparing a coating solution for forming the first layer, the addition amount of DISPERBYK-2055 as a dispersant is set at 28.8 g (relative to the organic pigment and the titanium oxide: 72.0% by weight, relative to the solid content: 25.6% by weight).

In the same manner as above, the visibility on a drape, identifiability from other color (blue, green and white) guide wires, and peeling resistance of the coating (adhesion property and strength) were evaluated. The results are shown in the following Table 2.

TABLE 2

|  | Example 6 | Example 7 | Example 4 | Example 8 | Example 9 | Example 10 |
| --- | --- | --- | --- | --- | --- | --- |
| Content of dispersant relative to organic pigment and titanium oxide (% by weight) | 3.8 | 4.8 | 8.0 | 12.0 | 25.0 | 72.0 |
| Content of dispersant relative to solid content (% by weight) | 1.8 | 2.2 | 3.7 | 5.4 | 10.7 | 25.6 |
| Visibility | ○ | ○ | ○ | ○ | ○ | ○ |
| Identifiability | ⊙ | ⊙ | ⊙ | ⊙ | ⊙ | ⊙ |
| Peeling resistance | ⊙ | ⊙ | ⊙ | ⊙ | ⊙ | ○ |

As shown in Table 2, all guide wires obtained from Examples 6 to 10 have high visibility on a blue non-woven fabric (drape) and excellent identifiability from the other color (blue, green and white) guide wires, and they also have an excellent adhesion property and strength of the coating.

The detailed description above describes embodiments of a medical device and method for fabricating or producing a medical device representing examples of the inventive medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
an elongated body possessing a distal-most end and a proximal-most end, the elongated body possessing a distal portion extending from the distal-most end of the elongated body towards the proximal-most end of the elongated body;
a first resin layer covering the proximal portion of the elongated body and not covering the distal portion of the elongated body, the first resin layer including a first fluororesin, organic pigment, and titanium oxide;
a second resin layer covering the first resin layer and not covering the distal portion of the elongated body, the second resin layer including a second fluororesin;
a composition of the first resin layer being different from a composition of the second resin layer;
the organic pigment containing at least one selected from the group consisting of an azo-based pigment, an anthraquinone-based pigment, a quinacridone-based pigment, a pyranthrone-based pigment, a perylene-based pigment, and a diketopyrrolopyrrole-based pigment; and
a content of the titanium oxide in the first resin layer being 100% by weight or more and 400% by weight or less relative to 100% by weight of a content of the organic pigment.

2. The medical device according to claim 1, wherein the first and second resin layers each possesses a distal-most end that is spaced proximally from the distal-most end of the elongated body by a distance of at least 300 mm.

3. The medical device according to claim 1, further comprising a wire member wound in a spiral shape in surrounding relation to the distal portion of the elongated body, the wire member that is wound in the spiral shape possessing a proximal-most end, the first and second resin layers each possessing a distal-most end spaced proximally from the proximal-most end of the wire member that is wound in the spiral shape.

4. The medical device according to claim 1, wherein the distal portion of the elongated body includes a first elongated portion, a second elongated portion and a third elongated portion, the first elongated portion possessing a distal-most end that is the distal-most end of the elongated body and also possessing a proximal-most end, the second elongated portion possessing a distal-most end directly connected to the proximal-most end of the first elongated portion and also possessing a proximal-most end, the third elongated portion possessing a distal-most end directly connected to the proximal-most end of the second elongated portion, the second elongated portion possessing a tapering shape that increases in outer diameter in a direction towards the proximal-most end of the second elongated portion, the third elongated portion possessing a constant outer diameter from the distal-most end of the third elongated portion towards the proximal-most end of the third elongated portion, the first and second resin layers each possessing a distal-most end spaced proximally from the proximal-most end of the second elongated portion of the distal portion of the elongated body.

5. The medical device according to claim 1, wherein the elongated body possesses an outer peripheral surface, the first resin layer directly contacting the outer peripheral surface of the elongated body, the first resin layer possessing an outer peripheral surface, the second resin layer overlying the outer peripheral surface of the first resin layer.

6. The medical device according to claim 1, wherein the elongated body possesses a proximal-most end portion that extends distally from the proximal-most end of the elongated body, the proximal-most end portion of the elongated body being a constant diameter proximal-most end portion possessing a constant outer diameter, the first resin layer covering the constant diameter proximal-most end portion of the elongated body.

7. The medical device according to claim 1, wherein a content of the organic pigment in the first resin layer is 5% by weight or more relative to a content of the first fluororesin.

8. The medical device according to claim 1, further comprising a dispersant in the first resin layer, and a content of the dispersant is 80% by weight or less relative to 100% by weight of a total content of the organic pigment and the titanium oxide.

9. The medical device according to claim 1, wherein the first fluororesin contains at least one selected from the group consisting of polytetrafluoroethylene (PTFE), tetrafluoroethylene-perfluoroalkyl vinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE).

10. The medical device according to claim 1, wherein the first resin layer possesses a thickness of 0.8 μm to 100 μm.

11. The medical device according to claim 1, wherein total thickness of the first and second resin layers is 1 μm to 200 μm.

12. The medical device according to claim 1, wherein a total content of the organic pigment and the titanium oxide in the second resin layer is less than 5% by weight relative to a solid content of the second layer.

13. The medical device according to claim 1, wherein the medical device is a guide wire.

14. The medical device according to claim 13, wherein the first and second resin layers are located between a position that is spaced 300 mm from a distal end of the guide wire toward a proximal end side and a proximal end of the guide wire.

15. The medical device according to claim 13, wherein the first and second resin layers are located between a position that is spaced 300 mm from a distal end of the guide wire toward a proximal end side and a position that is spaced 3500 mm from the distal end of the guide wire toward the proximal end side.

16. The medical device according to claim 1, wherein a total content of the organic pigment and titanium oxide in the second layer is less than 1% by weight relative to a solid content of the second layer and a content of particles other than the organic pigment and titanium oxide that are included in the second layer is less than 1% by weight.

17. A medical device comprising:
an elongated body and a resin layer covering at least a proximal portion of the elongated body,
the resin layer comprising: i) a first layer which includes a first fluororesin, an organic pigment, and titanium oxide; and ii) a second layer which is formed on the first layer and includes a second fluororesin,
the organic pigment containing at least one selected from the group consisting of an azo-based pigment, an anthraquinone-based pigment, a quinacridone-based pigment, a pyranthrone-based pigment, a perylene-based pigment, and a diketopyrrolopyrrole-based pigment, and
a content of the titanium oxide in the first layer being 100% by weight or more and 400% by weight or less relative to 100% by weight of a content of the organic pigment.

18. A method for producing a medical device comprising:
coating a first coating solution on at least a proximal portion of an elongated body to form a first coating film on the proximal portion of the elongated body, the first coating solution that is coated on the proximal portion of the elongated body to form the first coating film including a first fluororesin, organic pigment, and titanium oxide;
coating a second coating solution on the first coating film to form a second coating film, the second coating solution that is coated on the first coating film to form the second coating film including a second fluororesin; and
baking the elongated body coated with the first and second coating films at a temperature equal to or higher than a melting point of the first fluororesin and a melting point of the second fluororesin, wherein
the organic pigment contains at least one selected from the group consisting of an azo-based pigment, an anthraquinone-based pigment, a quinacridone-based pigment, a pyranthrone-based pigment, a perylene-based pigment, and a diketopyrrolopyrrole-based pigment, and
a content of the titanium oxide in the first layer is 100% by weight or more and 400% by weight or less relative to 100% by weight of a content of the organic pigment.

* * * * *